US010842395B2

(12) United States Patent
Schnall et al.

(10) Patent No.: US 10,842,395 B2
(45) Date of Patent: Nov. 24, 2020

(54) APPARATUS FOR MONITORING ARTERIAL PULSE WAVES IN DIAGNOSING VARIOUS MEDICAL CONDITIONS

(71) Applicant: Itamar Medical Ltd., Caesarea (IL)

(72) Inventors: Robert P. Schnall, Kiryat-Bialik (IL); Jacob Sheffy, Haifa (IL)

(73) Assignee: Itamar Medical Ltd., Caesarea (IL)

( * ) Notice: Subject to any disclaimer, the term of this patent is extended or adjusted under 35 U.S.C. 154(b) by 1256 days.

(21) Appl. No.: 14/360,635

(22) PCT Filed: Nov. 20, 2012

(86) PCT No.: PCT/IL2012/050466
§ 371 (c)(1),
(2) Date: May 26, 2014

(87) PCT Pub. No.: WO2013/076722
PCT Pub. Date: May 30, 2013

(65) Prior Publication Data
US 2014/0336517 A1 Nov. 13, 2014

Related U.S. Application Data

(60) Provisional application No. 61/563,574, filed on Nov. 24, 2011.

(51) Int. Cl.
*A61B 5/024* (2006.01)
*A61B 5/00* (2006.01)
*A61B 5/02* (2006.01)

(52) U.S. Cl.
CPC ...... *A61B 5/02444* (2013.01); *A61B 5/02007* (2013.01); *A61B 5/6826* (2013.01); *A61B 5/6829* (2013.01)

(58) Field of Classification Search
None
See application file for complete search history.

(56) References Cited

U.S. PATENT DOCUMENTS 2,438,901 A 4/1948 Coxe
3,104,661 A 9/1963 Halpern
(Continued)

FOREIGN PATENT DOCUMENTS

EP 0465345 1/1992
EP 465345 1/1992
(Continued)

OTHER PUBLICATIONS

Axtell et al. Assessing endothelial vasodilator function with the Endo-PAT 2000, 2010, JoVE. 44. http://www.jove.com/details.php?id=2167, including video demonstration.*
(Continued)

*Primary Examiner* — Michael R Bloch

(57) ABSTRACT

Apparatus for monitoring arterial pulse waves includes at least one separator ring receivable on at least one digit of a limb effective to tether a feed tube supplying a measuring device to a digit. Each separator ring is of a compliant material, of a non-interrupted tubular configuration, designed to avoid interference of blood supply to or from the digit to which it is applied, and of sufficient resilience and thickness to enable it to distance each adjacent digit from a digit mounted tubular socket probe so as to prevent contact between the tubular socket probe and adjacent digits, without interference to blood circulation, irrespective of the thickness of the digit on which the separator ring is received.

20 Claims, 10 Drawing Sheets

(56) References Cited

U.S. PATENT DOCUMENTS

| | | | |
|---|---|---|---|
| 3,156,237 A | 11/1964 | Edmark, Jr. | |
| 3,168,095 A * | 2/1965 | Magee | A61F 5/019 602/30 |
| 3,482,565 A | 12/1969 | Gowen | |
| 3,920,004 A | 11/1975 | Nakayama | |
| 4,030,485 A | 6/1977 | Warner | |
| 4,112,491 A | 9/1978 | Bugay | |
| 4,134,396 A | 1/1979 | Doll | |
| 4,204,545 A | 5/1980 | Yamakoshi | |
| 4,331,154 A | 5/1982 | Broadwater et al. | |
| 4,406,289 A | 9/1983 | Wesseling et al. | |
| 4,437,470 A | 3/1984 | Prost | |
| 4,515,166 A | 5/1985 | Timm | |
| 4,548,211 A | 10/1985 | Marks | |
| 4,664,651 A | 5/1987 | Weinshenker et al. | |
| 4,677,984 A | 7/1987 | Sramek | |
| 4,685,464 A | 8/1987 | Goldberger et al. | |
| 4,779,629 A | 10/1988 | West et al. | |
| 4,821,734 A | 4/1989 | Koshino | |
| 4,836,219 A | 6/1989 | Hobson et al. | |
| 4,846,189 A | 7/1989 | Sun | |
| 4,848,361 A | 7/1989 | Penney et al. | |
| 4,860,759 A | 8/1989 | Kahn et al. | |
| 4,862,895 A | 9/1989 | Yamasawa et al. | |
| 4,907,594 A | 3/1990 | Muz | |
| 4,926,867 A | 5/1990 | Kanda et al. | |
| 4,967,758 A | 11/1990 | Masciarotte | |
| 5,031,675 A | 7/1991 | Lindgren | |
| 5,065,749 A | 11/1991 | Hasebe et al. | |
| 5,101,831 A | 4/1992 | Koyama et al. | |
| 5,111,817 A | 5/1992 | Clark et al. | |
| 5,140,990 A | 8/1992 | Jones et al. | |
| 5,179,956 A | 1/1993 | Harada et al. | |
| 5,188,108 A | 2/1993 | Secker | |
| 5,238,000 A | 8/1993 | Niwa | |
| 5,280,791 A | 1/1994 | Lavie | |
| 5,309,908 A | 5/1994 | Friedman et al. | |
| 5,337,744 A | 8/1994 | Branigan | |
| 5,365,924 A | 11/1994 | Erdman | |
| 5,398,682 A | 3/1995 | Lynn | |
| 5,438,986 A | 8/1995 | Disch et al. | |
| 5,452,717 A | 9/1995 | Branigan et al. | |
| 5,542,421 A | 8/1996 | Erdman | |
| 5,566,677 A | 10/1996 | Raines et al. | |
| 5,605,151 A | 2/1997 | Lynn | |
| 5,620,001 A | 4/1997 | Byrd et al. | |
| 5,667,837 A | 9/1997 | Broomhead et al. | |
| 5,669,390 A | 9/1997 | McCormick et al. | |
| 5,740,943 A | 4/1998 | Shields et al. | |
| 5,853,371 A | 12/1998 | Inukai et al. | |
| 5,891,023 A | 4/1999 | Lynn | |
| 5,917,415 A | 6/1999 | Atlas | |
| 6,115,621 A | 9/2000 | Chin | |
| 6,120,459 A | 9/2000 | Nitzan et al. | |
| 6,151,516 A | 11/2000 | Kiani-Azarbayjany et al. | |
| 6,152,881 A | 11/2000 | Raines et al. | |
| 6,162,188 A | 12/2000 | Barnea | |
| 6,179,159 B1 | 1/2001 | Gurley | |
| 6,223,064 B1 | 4/2001 | Lynn et al. | |
| 6,319,205 B1 * | 11/2001 | Goor | A61B 5/02007 600/481 |
| 6,322,515 B1 | 11/2001 | Goor et al. | |
| 6,338,719 B1 | 1/2002 | Drzewiecki et al. | |
| 6,342,039 B1 | 1/2002 | Lynn et al. | |
| 6,343,223 B1 | 1/2002 | Chin et al. | |
| 6,375,620 B1 | 4/2002 | Oser et al. | |
| 6,461,305 B1 | 10/2002 | Schnall | |
| 6,478,745 B2 | 11/2002 | Nakagawa et al. | |
| 6,488,633 B1 | 12/2002 | Schnall | |
| 6,553,243 B2 | 4/2003 | Gurley | |
| 6,654,628 B1 | 11/2003 | Silber et al. | |
| 6,719,704 B2 | 4/2004 | Narimatsu et al. | |
| 6,748,252 B2 | 6/2004 | Lynn et al. | |
| 6,760,608 B2 | 7/2004 | Lynn | |
| 6,916,289 B2 | 7/2005 | Schnall | |
| 6,939,304 B2 | 9/2005 | Schnall et al. | |
| 7,374,540 B2 | 5/2008 | Schnall | |
| 7,819,811 B2 | 10/2010 | Schnall | |
| 2003/0004423 A1 | 1/2003 | Lavie et al. | |
| 2003/0050541 A1 | 3/2003 | Wuori | |
| 2003/0109772 A1 | 6/2003 | Mills | |
| 2004/0044290 A1 | 3/2004 | Ward et al. | |
| 2004/0092832 A1 * | 5/2004 | Schnall | A61B 5/02007 600/490 |
| 2004/0116787 A1 | 6/2004 | Schnall | |
| 2006/0104824 A1 | 5/2006 | Schnall | |
| 2008/0077024 A1 | 3/2008 | Schnall | |
| 2010/0004546 A1 | 1/2010 | Tanaka et al. | |
| 2011/0124979 A1 * | 5/2011 | Heneghan | A61B 5/024 600/301 |

FOREIGN PATENT DOCUMENTS

| | | |
|---|---|---|
| JP | 05-056902 | 3/1993 |
| WO | WO 98/04182 | 2/1998 |
| WO | WO 99/63884 | 12/1999 |
| WO | WO 00/74551 | 12/2000 |
| WO | WO 01/03569 | 1/2001 |
| WO | WO 01/17426 | 3/2001 |
| WO | WO 01/64101 | 9/2001 |
| WO | WO 02/24053 | 3/2002 |
| WO | WO 02/34105 | 5/2002 |
| WO | WO 02/073948 | 9/2002 |
| WO | WO 02/080752 | 10/2002 |
| WO | WO2004/041079 | 5/2004 |
| WO | WO 2004/086963 | 10/2004 |
| WO | WO 2006/030441 | 3/2006 |
| WO | WO 2013/076722 | 5/2013 |

OTHER PUBLICATIONS

Notice of Reason for Rejection dated Sep. 23, 2016 From the Japan Patent Office Re. Application No. 2014-542995 and Its Translation Into English.
International Preliminary Report on Patentability dated Jun. 5, 2014 From the International Bureau of WIPO Re. Application No. PCT/IL2012/050466.
Official Action dated Nov. 15, 2007 From the US Patent and Trademark Office Re.: U.S. Appl. No. 10/471,580.
Official Action dated Jun. 28, 2007 From the US Patent and Trademark Office Re.: U.S. Appl. No. 10/471,580.
Advisory Action Before the Filing of an Appeal Brief dated Nov. 4, 2011 From the US Patent and Trademark Office Re. U.S. Appl. No. 11/662,610.
Communication Pursuant to Article 94(3) EPC dated Jul. 7, 2010 From the European Patent Office Re. Application No. 05779418.2.
Communication Pursuant to Article 94(3) EPC dated Mar. 7, 2008 From the European Patent Office Re.: Application No. 00937145.1.
Communication Pursuant to Article 94(3) EPC dated Jun. 10, 2011 From the European Patent Office Re.: Application No. 03810573.0.
Communication Pursuant to Article 94(3) EPC dated Apr. 21, 2010 From the European Patent Office Re.: Application No. 03810573.0.
Communication Pursuant to Article 94(3) EPC dated Jul. 21, 2010 From the European Patent Office Re. Application No. 01982669.2.
Communication Pursuant to Article 94(3) EPC dated Jan. 29, 2014 From the European Patent Office Re. Application No. 05779418.2.
Communication Pursuant to Article 96(2) EPC dated Mar. 12, 2007 From the European Patent Office Re.: Application No. 01910113.8.
Communication Pursuant to Article 96(2) EPC dated Jul. 31, 2007 From the European Patent Office Re.: Application No. 00937145.1.
Communication Under Rule 71(3) EPC dated Apr. 13, 2012 From the European Patent Office Re.: Application No. 03810573.0.
Examiner's Answer dated Jun. 15, 2012 Before the Board of Patent Appeals and Interferences From the US Patent and Trademark Office Re. U.S. Appl. No. 11/662,610.
Examiner's Answer dated May 15, 2012 Before the Board of Patent Appeals and Interferences From the US Patent and Trademark Office Re. U.S. Appl. No. 11/662,610.

(56) References Cited

OTHER PUBLICATIONS

Examiner's Report dated Jun. 21, 2005 From the Australian Government, IP Australia Re.: Application No. 2002214210.
International Preliminary Examination Report dated May 20, 2003 From the International Preliminary Examining Authority Re.: Application No. PCT/IL00/00403.
International Preliminary Report on Patentability dated Mar. 29, 2007 From the International Bureau of WIPO Re.: Application No. PCT/IL2005/000993.
International Search Report and the Written Opinion dated Mar. 19, 2013 From the International Searching Authority Re. Application No. PCT/IL2012/050466.
International Search Report dated Jan. 4, 2001 From the International Searching Authority Re.: Application No. PCT/IL00/00403.
Notice of Allowance dated May 19, 2010 From the US Patent and Trademark Office Re.: U.S. Appl. No. 10/195,464.
Notice of Allowance dated Jul. 22, 2010 From the US Patent and Trademark Office Re.: U.S. Appl. No. 10/533,970.
Notice of Panel Decision From Pre-Appeal Brief Review dated Jan. 27, 2012 From the US Patent and Trademark Office Re. U.S. Appl. No. 11/662,610.
Official Action dated May 12, 2006 From the US Patent and Trademark Office Re.: U.S. Appl. No. 10/019,684.
Official Action dated Jul. 13, 2007 From the US Patent and Trademark Office Re.: U.S. Appl. No. 10/195,464.
Official Action dated Apr. 15, 2010 From the US Patent and Trademark Office Re.: U.S. Appl. No. 10/533,970.
Official Action dated Jan. 18, 2007 From the US Patent and Trademark Office Re.: U.S. Appl. No. 10/195,464.
Official Action dated Jan. 18, 2011 From the US Patent and Trademark Office Re. U.S. Appl. No. 11/662,610.
Official Action dated May 18, 2005 From the US Patent and Trademark Office Re.: U.S. Appl. No. 10/019,684.
Official Action dated Oct. 20, 2005 From the US Patent and Trademark Office Re.: U.S. Appl. No. 10/019,684.
Official Action dated Sep. 23, 2009 From the US Patent and Trademark Office Re.: U.S. Appl. No. 10/533,970.
Official Action dated Aug. 26, 2011 From the US Patent and Trademark Office Re. U.S. Appl. No. 11/662,610.
Official Action dated Jun. 29, 2004 From the US Patent and Trademark Office Re.: U.S. Appl. No. 10/019,684.
Response dated Jul. 14, 2010 to Official Action dated Apr. 15, 2010 From the US Patent and Trademark Office Re.: U.S. Appl. No. 10/533,970.
Requisition by the Examiner dated May 10, 2012 From the Canadian Intellectual Property Office Re. Application No. 2,505,136.
Requisition by the Examiner dated Aug. 17, 2007 From the Canadian Intellectual Property Office Re.: Application No. 2,375,470.
Requisition by the Examiner dated Jan. 19, 2010 From the Canadian Intellectual Property Office Re.: Application No. 2,424,389.
Requisition by the Examiner dated Aug. 24, 2011 From the Canadian Intellectual Property Office Re. Application No. 2,505,136.
Requisition by the Examiner dated May 25, 2012 From the Canadian Intellectual Property Office Re. Application No. 2,580,399.
Requisition by the Examiner dated Dec. 31, 2010 From the Canadian Intellectual Property Office Re. Application No. 2,441,973.
Requisition by the Examiner dated Jan. 31, 2014 From the Canadian Intellectual Property Office Re. Application No. 2,580,399.
Supplementary European Search Report and the European Search Opinion dated Jan. 25, 2008 From the European Patent Office Re. Application No. 05779418.2.
Supplementary European Search Report dated Feb. 1, 2010 From the European Patent Office Re.: Application No. 03810573.0.
Supplementary European Search Report dated Aug. 11, 2008 From the European Patent Office Re.: Application No. 01982669.2.
Supplementary European Search Report dated Oct. 16, 2008 From the European Patent Office Re.: Application No. 00946244.1.
Translation of Decision of Rejection dated Sep. 2, 2011 From the Japanese Patent Office Re. Application No. 2001-563003.
Translation of Notice of Reason for Rejection dated Jan. 5, 2007 From the Japanese Patent Office Re.: Application No. 2002-537165.
Translation of Notice of Reason for Rejection dated May 7, 2010 From the Japanese Patent Office Re. Application No. 2001-501092.
Translation of Notice of Reason for Rejection dated Mar. 8, 2011 From the Japanese Patent Office Re. Application No. 2001-563003.
Translation of Notice of Reason for Rejection dated Aug. 13, 2010 From the Japanese Patent Office Re. Application No. 2001-563003.
Translation of Notice of Reason for Rejection dated Sep. 14, 2012 From the Japanese Patent Office Re. Application No. 2001-563003.
Written Opinion dated Nov. 5, 2001 From the International Preliminary Examining Authority Re.: Application No. PCT/IL00/00403.
Axtell et al. "Assessing Endothelial Vasodilator Function With the Endo-PAT 2000", Journal of Visualized Experiments, 44: e2167-1-e2167-5, Oct. 2010.
Brown et al. "Filling and Emptying of the Low-Pressure Blood Vessels of the Human Forearm", Journal of Applied Physiology, 21(2): 573-582, Mar. 1966.
Celermajer et al. "Non-Invasive Detection of Endothelial Dysfunction in Children and Adults at Risk of Atherosclerosis", The Lancet, XP008007238, 340(8828): 1111-1115, Nov. 7, 1992. Sections 'Patients and Methods', 'Discussion'.
Dorlas et al. "Photo-Electric Plethysmography as A Monitoring Device in Anaesthesia. Application and Interpretation", British Journal of Anaesthesia, 57(5): 524-530, 1985. Abstract.
Edwards et al. "The Cutaneous Vasoconstrictor Response to Venous Stasis Is Normal in Subjects With Primary Raynaud's Disease", Clinical Autonomic Research, 9(5): 255-262, 1999. Abstract.
Guilleminault et al. "A Cause of Excessive Daytime Sleepiness. The Upper Airway Resistance Sindrome", Chest, 104(3): 781-787, 1993. Abstract.
Hedblad et al. "Low Pulse-Wave Amplitude During Reactive Leg Hyperaemia: An Independent, Early Marker for Ischaemic Heart Disease and Death. Results From the 21-Year Follow-Up of the Prospective Cohort Study 'Men Born in 1914', Malm?, Sweden", Journal of Internal Medicine, 236: 161-168, 1994. Abstract.
Jain et al. "Prognostic Implications of Mental Stress-Induced Silent Left Ventricular Dysfunction in Patients With Stable Angina Pectoris", The American Journal of Cardiology, 76(1): 31-35, 1995. Abstract.
Jiang et al. "Mental Stress-Induced Myocardial Ischemia and Cardiac Events", JAMA, 275(21): 1651-1656, 1996. Abstract.
Joyner et al. "From Belfast to Mayo and Beyond: The Use and Future of Plethysmography to Study Blood Flow in Human Limbs", Journal of Applied Physiology, 91: 2431-2441, Dec. 2001.
Kuo et al. "Endothelium-Dependent, Flow-Induced Dilation of Isolated Coronary Arterioles", American Journal of Physiology, 259(4 Pt.2): H1063-H1070, 1990. Abstract.
Kurata et al. "Electrocardiographically and Symptomatically Silent Myocardial Ischemia During Exercise Testing", Japanese Circulation Journal, 55(9): 825-834, 1991. Abstract.
Ludmer et al. "Paradoxical Vasoconstriction Induced by Acetylcholine in Atherosclerotic Coronary Arteries", New England Journal of Medicine, 315(17): 1046-1051, 1986. Abstract.
Nijboer et al. "Comparison of Phetysmograms Taken From Finger and Pinna During Anaesthesia", British Journal of Anaesthesia, 57(5): 531-534, 1985. Abstract.
Ogren et al. "Plethysmographic Pulse Wave Amplitude and Future Leg Arteriosclerosis", Atheriosclerosis, 113(91): 55-62, 1995. Abstract.
Pillar et al. "Paradoxical Effects of Hypoglycemia on Sleep Regulation in Children With Type 1 Diabetes Mellitus", Journal of Sleep Research, 11(Suppl.1): 1-260, 359 O, p. 1-13, 2002.
Raymond et al. "Combined Index of Heart Rate Variability and Oximetry in Screening for the Sleep Apnoea/Hypopnoea Syndrome", Journal of Sleep Research, 12(1): 53-61, 2003. Abstract.
Rozanski et al. "Impact of Psychological Factors of the Pathogenesis of Cardiovascular Disease and Implications for Therapy", Circulation, 99: 2192-2217, 1999.
Schnall et al. "A Rapid Noninvasive Blood Pressure Measurement Method for Discrete Value and Full Waveform Determination", Journal of Applied Physiology, 80(1): 307-314, 1996. Abstract.

(56) References Cited

OTHER PUBLICATIONS

Wallace "Does the Hydrostatic Pressure of the Water in a Venous Occlusion Plethysmograph Affect the Apparent Rate of Blood Flow to the Forearm?", The Journal of Physiology, 143: 380-385, 1958.
Wang et al. "Increased Aortic Stiffness Assessed by Pulse Wave Velocity in Apolipoprotein E-Deficient Mice", American Journal of Physiology—Heart and Circulatory Physiology, XP002489146, 278: H428-H434, Feb. 2000. Section 'Discussion'.
Webster et al. "Definition of Sponge", Webster's II New Riverside University Dictionary, p. 1, 1984.

* cited by examiner

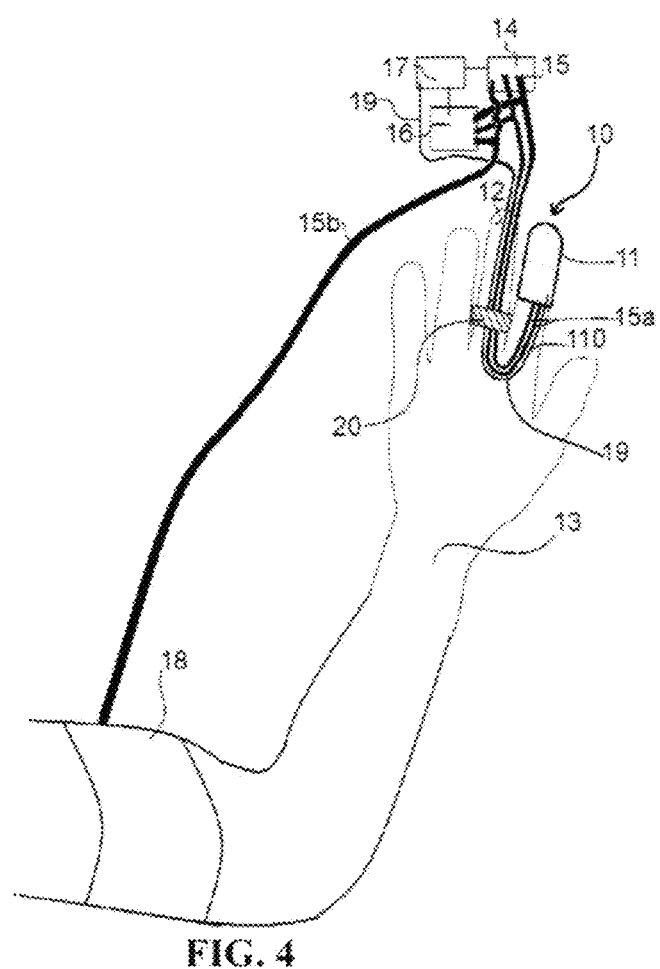

Ⓐ corrected ratio = (704/701)/(703/702)

Ⓑ baseline amplitude corrected ratio = Ⓐ × a × log (701) + b

Ⓒ temporally adjusted baseline amplitude corrected ratio = Ⓐ × a × log (701*703/702) + b Ⓓ tissue volume adjusted baseline amplitude corrected ratio = Ⓐ × a × log (701/tissue vol/ref vol) + b Ⓔ pulse pressure adjusted baseline amplitude corrected ratio = Ⓐ × a × log (701/ pulse press/ ref pulse press) + b

APPARATUS FOR MONITORING ARTERIAL PULSE WAVES IN DIAGNOSING VARIOUS MEDICAL CONDITIONS

RELATED APPLICATIONS

This application is a National Phase of PCT Patent Application No, PCT/IL2012/050466 having International filing date of Nov. 20, 2012 which claims the benefit of priority under 35 USC § 119(e) of U.S. Provisional Patent Application No. 61/563,574, filed on Nov. 24, 2011. The contents of the above applications are all incorporated by reference as if fully set forth herein in their entirety.

FIELD AND BACKGROUND OF THE INVENTION

The present invention relates to apparatus for monitoring arterial pulse waves in diagnosing various medical conditions. The invention is particularly useful in relation to the methods and apparatus for measuring the peripheral arterial tone of a subject, such as described in U.S. Pat. Nos. 6,319,205, 6,322,515, 6,488,633, 6,939,304, 7,374,540 and 7,819,811, and US Patent Application No. 20080077024, (all incorporated herein by reference), and is therefore described below with respect to such apparatus and methods, but it will be appreciated that the invention could also be advantageously used in other apparatus and methods.

The above-identified U.S. patents and patent application disclose apparatus including various probe constructions and methods for the noninvasive detection of medical conditions of a subject, particularly by monitoring changes in the peripheral arterial tone, as manifested by changes in the pulsatile arterial blood volume in a body part, e.g., a digit (finger or toe) of the subject. The various medical conditions detected by such probes, as described therein, include myocardial ischemia, sleep apnea, endothelial dysfunction (ED), sleep disorders, sleep stages, mental stress, sympathetic nervous system reactivity, blood pressure, etc. The preferred embodiments described therein are particularly useful for monitoring peripheral arterial tone in a subject's finger, and for this purpose, they include pressurizing means for applying a static pressure field substantially uniformly around the distal end of the subject's finger, including its terminal-most extremity. The pressure field is of a predetermined magnitude sufficient to substantially prevent distention of the venous vasculature, uncontrolled venous backflow and retrograde shockwave propagation into the distal end of the finger, and to partially unload the wall tension of, but not to occlude, the arteries in the distal end of the finger when at heart level or below. The probe sensor senses changes in the distal end of the subject's digit (finger or toe), related to changes in volume therein due to pulsatile changes in instantaneous blood volume related to arterial tone.

Further particulars as to the construction of such probes, and the various medical conditions for which they may be used, are available in the above-identified U.S. patents and patent application.

OBJECTS AND BRIEF SUMMARY OF THE INVENTION

An object of the present invention is to improve such apparatus and diagnostic method in one or more of the following respects: in the performance and/or accuracy of the apparatus and method, in the interpretation of the data acquired, and/or in the ease of using the apparatus or implementing the method.

Probably most relevant to the present invention is U.S. Pat. No. 6,939,304 (hereinafter the '304 patent) which relates to apparatus for monitoring arterial pulse waves of a subject having a pair of upper limbs, a pair of lower limbs, and a plurality of digits on each of said limbs comprising:

at least one tubular socket probe for application to at least the distal phalanx of a digit, including the outer most tip of said plurality of digits, on one limb;

a pressure applicator for applying a static pressure field via a fluid conducting feed tube, to said distal phalanges in said one limb; and a measuring device carried at least in part by said tubular socket probe for measuring arterial pulse wave signals resulting from arterial pulse waves flowing through said distal phalanx in said at least one digit in said one limb.

Preferably, the static pressure field is applied by a thimble shaped probe including an end cap enclosing the distal most phalanx, and a contiguous annular cuff.

According to a broad aspect of the present invention, such apparatus is characterized in that said apparatus further comprises a plurality of separator rings at least one of which is receivable on at least one of said digits securing thereto said pressure feed tube to tether said fluid feed tube to said digit, said at least one separator ring being of a compliant material, of a non-interrupted tubular configuration, and of sufficient resilience and thickness to enable it to distance an applied tubular socket probe from an adjacent digit so as to prevent contact between said tubular socket probe and said adjacent digit, irrespective of the thickness of the digit on which the separator ring is received.

More particularly, the pressure applicator is configured to apply a static pressure field, via the fluid feed tube, to said at least distal phalanx of the at least one digit, and an interrupted occluding pressure field to a region between said at least one distal phalanx and the subject's heart; and this apparatus further comprises a processor for calculating said occluding and static pressure fields in response to the output of said at least one measuring device.

According to another aspect of the present invention, the interrupted occlusion pressure field is to be applied by an occluding cuff on one of said limbs in said one pair limbs; and a said separator ring is designed to be applied to the digit receiving said probe, or to two digits straddling the digit receiving said probe.

According to one feature of the present invention, the inner surface of each separator ring is formed with a plurality of longitudinally-extending, circumferentially spaced ribs, with intervening gaps effective to reduce interference of the separator ring with blood supply to or from the digit to which it is applied, irrespective of the size of said digital phalanx. This feature thus causes the separator ring to engage the perimeter of the finger with multiple wedge-like projections at evenly spaced intervals with interspersed gaps, to apply localized force of a level:

a) to ensure that the flow of both venous and arterial blood is not adversely affected, b) to ensure an evenly spaced coupling to the body surface over the perimeter of the digit, c) to adapt it to a range of digit sizes covering the normal anatomical range in the population, without applying inconvenient pressure to the digit, and d) to facilitate a stable and robust link to the digit.

According to another feature of the invention, the fluid conducting feed tube is connected to, or passes through, a bore formed longitudinally through each separator ring laterally of said longitudinally-extending, circumferentially-spaced ribs, on the side of said separator ring to face the outer dorsal surface of the digit on which the distal probe is applied so as not only to support and tether the feed tube, but also to elevate it above the body surface.

According to a still further feature, said apparatus further comprises a mounting member for the fluid conducting pressure feed tube designed to be removably attachable to the respective tubular socket probe so as to form a stable but reversible airtight seal between said tube and the tubular socket probe, and locking elements which interact to anchor and lock said elements in a stable manner.

According to yet another feature, the apparatus further comprises at least one limb support for supporting said one limb and for temporarily supporting the tubular probe during its application to the digit.

According to another feature, the processor controls said occluding and static pressure fields by monitoring said arterial pulse waves for a predetermined time period before each occlusion, during each occlusion, and after each occlusion.

According to another feature, the processor normalizes the signals received from the measuring device to the tissue volume of the respective digit.

According to another feature, the processor normalizes the signals received from an occluded site with those simultaneously recorded from a non-occluded site, and determines a response ratio.

According to still another feature, the processor corrects the response ratio according to the signal amplitude before occlusion.

The invention is particularly, but not exclusively useful in cases wherein the pressure applicator applies a pressure sufficient to substantially prevent venous pooling and to partially unload wall tension of, but not to occlude, the arteries in the respective digit including its distal extremity, and especially wherein it provides an output indicating the Augmentation Index of the subject.

Further features and advantages of the invention will be apparent from the description below.

BRIEF DESCRIPTION OF THE DRAWINGS

The invention is herein described, by way of example only, with reference to the accompanying drawings, wherein:

FIGS. 4-7 illustrate four further variations in the apparatus of FIGS. 1-3;

FIG. 10 illustrates a further construction of separator ring in accordance with the present invention;

FIGS. 11-14 illustrate another variation constructed in accordance with the present invention wherein FIG. 11 illustrates the probe, FIG. 12 illustrates the tube holder, FIG. 13 illustrates the assembly of probe and tube holder, and FIG. 14 illustrates the assembly and separator ring;

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED
EMBODIMENTS OF THE INVENTION

FIGS. 1-4 schematically illustrate four variations in one form of prior art apparatus for monitoring arterial pulse waves of a subject showing improvements according to the present invention. Such a prior art apparatus is described, for example, in the above-cited U.S. Pat. No. 6,939,304 (the '304 patent), and the first three of such variations are illustrated particularly in FIGS. 3-5 of that patent.

Figure 1:
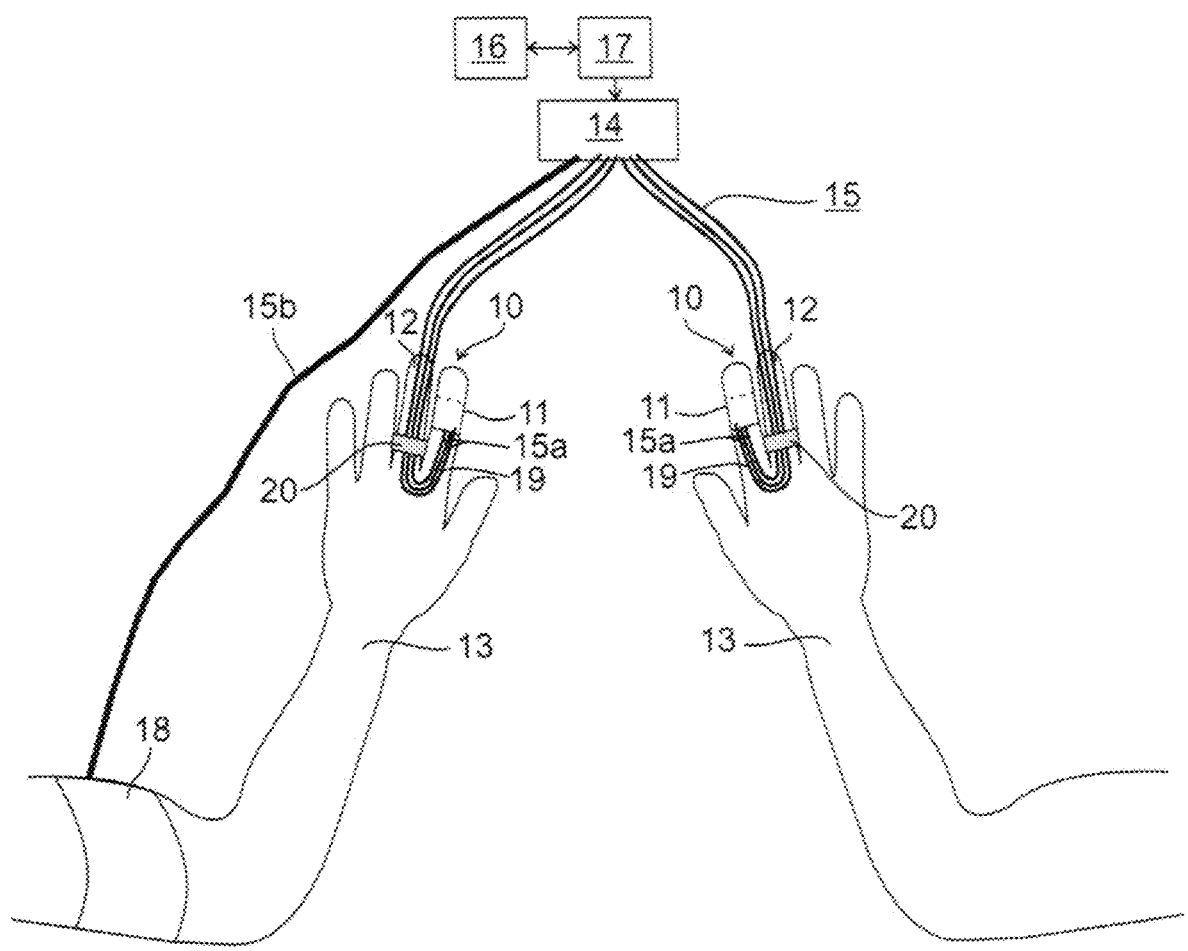
FIGS. 1-3, illustrate three variations of apparatus showing improvements according to the present invention.

Briefly, the prior art apparatus illustrated in FIG. 1 includes a pressure applicator, generally designated 10, having a tubular socket probe 11 for receiving the distal phalanges of a digit 12 on a limb 13 of the subject's body; and a pressure source 14 for applying, via branch 15a of feed tube 15, a static pressure field generally around at least the distal phalanx, including the distal extremity of the finger 12, when received within the tubular socket probe, and an interrupted occluding pressure field to a region between that at least distal phalanx and the subjects heart, or within the said pressure applicator 10 itself. The tubular socket probe 11 further includes a pulse wave measuring device, schematically indicated at 16, for measuring pulse wave signals resulting from arterial blood pulse waves in the at least distal phalanx, and a processor 17 for receiving signals from the measuring device and for controlling the occluding and static pressure fields. The interrupted occluding pressure field is produced by an occluding cuff, shown at 18 in FIG. 1.

As described in the above-cited U.S. Patents, such probes are useful in detecting a wide variety of medical conditions, and may utilize numerous types of blood pulse sensors, other than volumetric change measurement, such as optical density or surface reflectivity devices, pulse oximeters, electrical resistivity devices, Doppler ultrasound devices, laser Doppler devices or other flow meter devices, segmental plethysmographs, circumferential strain gauge devices, optical plethysmographs, isotope washout devices, thermal washout devices, electromagnetic devices and any other sensors which are affected by a change in finger geometry or red blood cell alignment or flux associated with pulsatile volume changes, Hall effect sensors, and the like.

Figure 2:
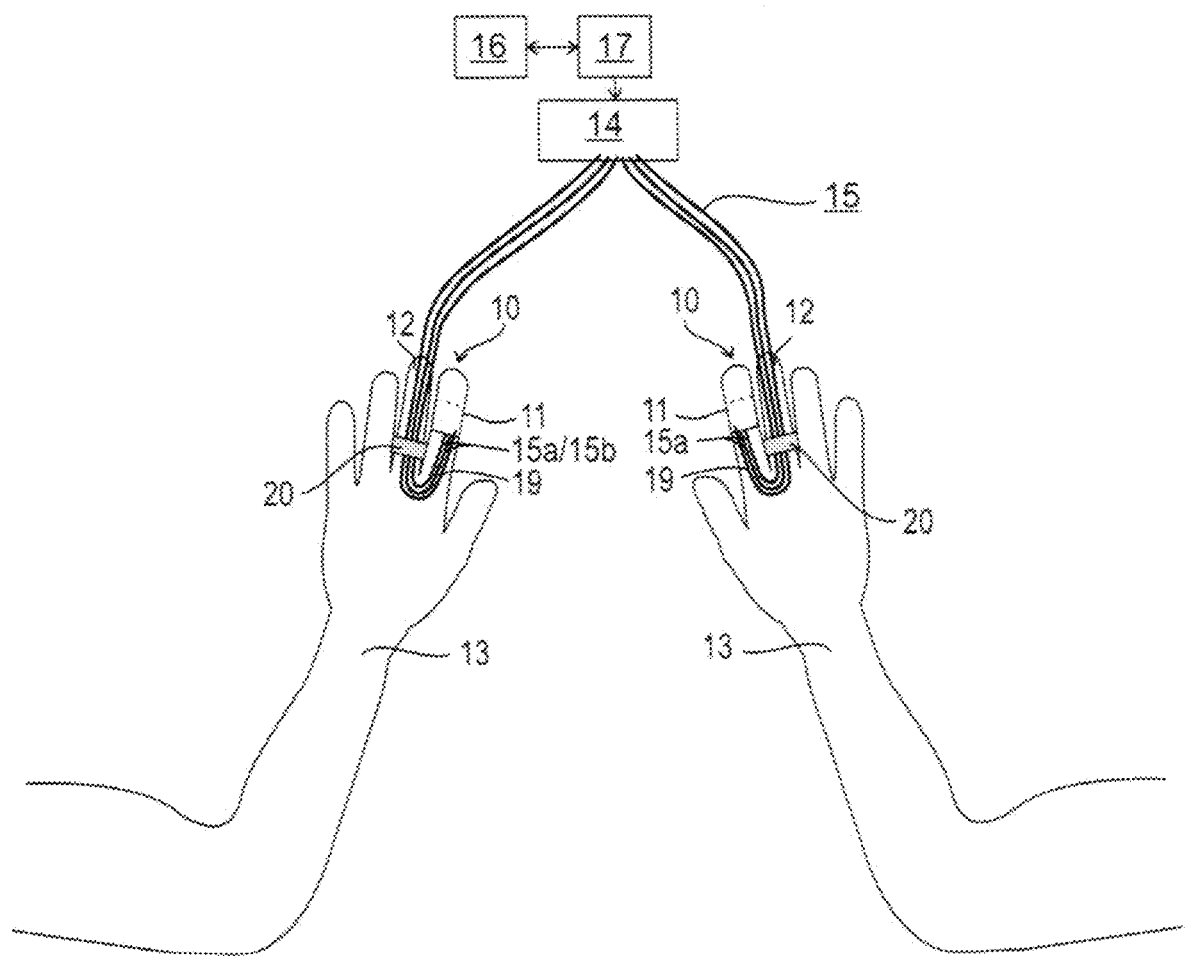
Figure 3:
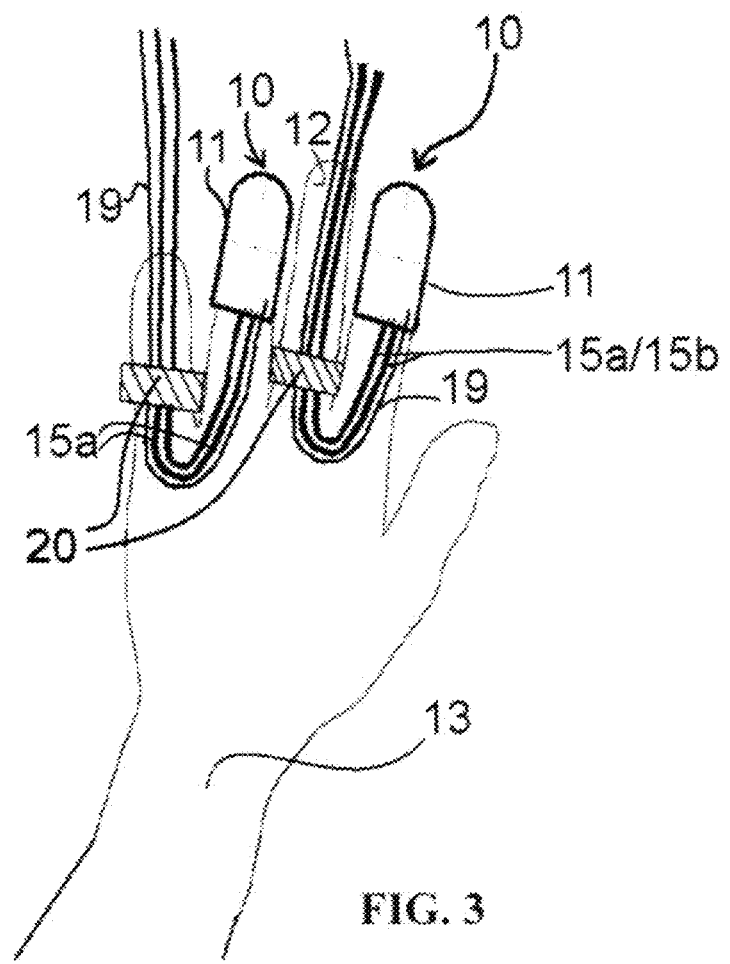

FIGS. 1-3 illustrate one improvement of the present invention in the provision of a separator ring 20 releasably or permanently securing thereto the at least one fluid pressure feed tube branch or branches 15a/15b to tether the measuring device 16 to a finger 12, and to the probe 10. Separator ring 20 is of a compliant material, of a non interrupted tubular configuration and of sufficient resiliency and thickness to enable it to distance distal phalanges of different thicknesses from the distal phalanx of an adjacent digit.

FIG. 1 illustrates an arrangement for determining the arterial response to a predetermined period of arterial occlusion. In the apparatus depicted in FIG. 1, probes 11 are applied to digits of the respective right and left sides of the arms 13, or of the legs. During the course of the test, one side only is subjected to a period of arterial occlusion effected by the application of a super systolic pressure field applied via cuff 18, while the opposite side serves as an un-occluded control, and the simultaneously recorded data derived from the respective probes is processed in the manner described below with respect to FIG. 17.

FIG. 2 illustrates a variation of the above described arrangement; instead of the occlusion pressure field being applied by cuff 18, it is applied directly to the at least distal phalanx by one of the probes 11, via the pressure feed tubes 15. In this case, the pressure tubes designated as 15*a*/15*b*, conduct the occluding pressure such that during the period of occlusion, a supra-systolic pressure field equivalent to that supplied by cuff 18 in FIG. 1, is applied within the probe, while during the rest of the test, the same non-occluding static pressure field is applied to both probes.

FIG. 3 illustrates a further setup, identical to that illustrated in FIG. 2, except that in this case, digits of the same limb serve as the respective occluded and un-occluded sites.

FIG. 4 illustrates a further arrangement for determining the arterial response to a predetermined period of arterial occlusion. In this apparatus depicted in FIG. 4, a probe 11 is applied to one digit 12 (e.g. the index finger) on one arm 13 of the subject, and the interrupted occluding pressure field is applied by cuff 18 to the upper end of arm 13. The static pressure field is applied by the probe 11, and the separator ring 20 is designed to be received on an adjacent digit 12 (e.g. finger) to that receiving the probe.

FIGS. 5 and 6 illustrate arrangements similar to that of FIG. 4, except that in FIG. 5, the separator ring 20 is spaced near the probe 11, and in FIG. 6, the separator ring is applied against the probe.

FIG. 7 illustrates a still further arrangement wherein two separator rings are applied to the two fingers straddling the finger the probe 11.

Figure 8:
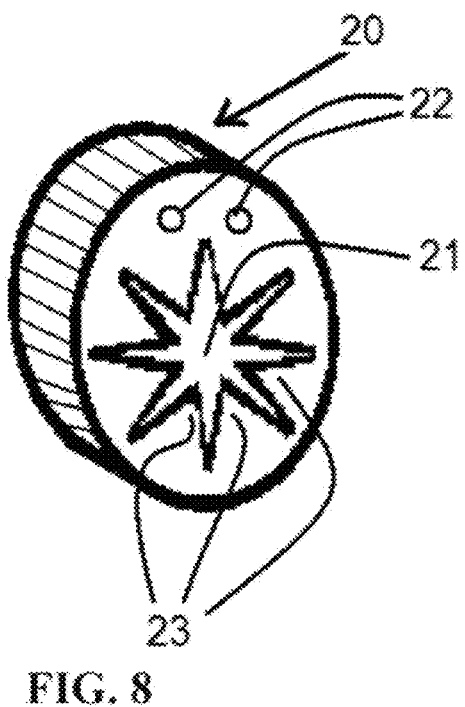
FIGS. 8-10 illustrate three forms of separator ring constructed in accordance with the invention for use in the apparatus of FIGS. 1-7.

As shown in FIG. 8, separator ring 20 may be in the form of a torus with a rectangular cross section 20. It is of a hollow tubular construction, to define an inner lumen 21 for receiving the digit, (e.g. finger), of the subject's body, and is formed with a plurality of holes 22 defining passageways for receiving the tubes 15 (FIG. 1) supplying the pressurized air to the tubular probe 10. FIG. 8 also illustrates the longitudinally extending, circumferentially spaced ribs defining the multiple wedge-like projections 23 at evenly spaced intervals, effective to ensure that the flow of both venous and arterial blood are not adversely affected, while providing an evenly spaced coupling to the body surface over the perimeter of the digit. The separator ring is applicable to digits of a range of sizes spanning the normal anatomical range in the population.

Figure 9:
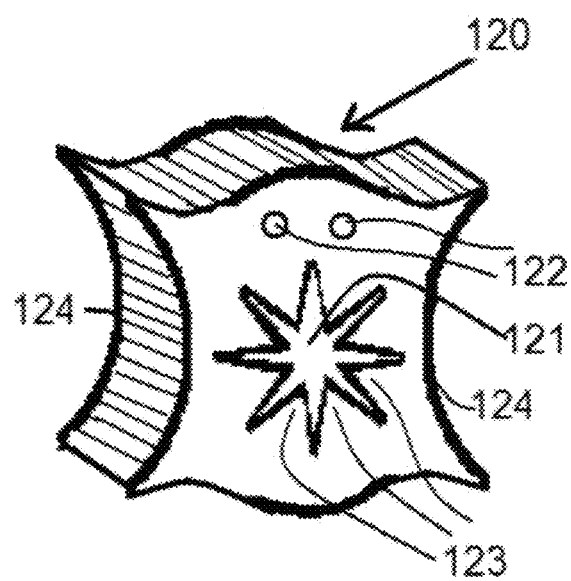

FIG. 9 illustrates a modification in which the separator ring, generally designated 120, is in the form of a torus with a rectangular cross section, and is formed with the same elements 121, 122 and 123, corresponding to elements 21, 22 and 23, respectively, in FIG. 8, but is further formed on its outer surface with grooves 124 on either or both sides facing neighboring finger/fingers, to accommodate the adjacent finger/fingers (or toe/toes) 12, as illustrated in FIGS. 4-7. Such grooves aid in stabilizing the adjacent finger/fingers, thus further reducing the potential movement of fingers and improve signal stability.

The separator ring of FIG. 8 or FIG. 9 may be placed on the proximal phalanx of a finger adjacent to the finger upon which the probe 11 is placed, or on the same finger either at a distance to the probe, or in direct contiguity to it, while the probe 11 is placed over the distal phalanges of the finger. As can also be seen, tubes 15 supplying the probe are supported by the separator ring and are elevated above the body surface. The tubes may form an arc between the probe and separator, or follow a straight path, as shown.

It will thus be seen that although an air tube tethering function was described in U.S. Pat. No. 6,319,205, as illustrated in FIG. 8 therein, the described means for achieving this objective held the tubes in place immediately atop the instrumented finger. In the present application, this function is preferably effected in an integrated manner with the novel digit separator 120, wherein the tube tethering feature is integrated with the digit separator, and further serves to elevate the tubes above the tissues, thereby avoiding undesirable perturbation of the tubes by contact with the body. This may be achieved by using the tube holes formed within the matrix of the finger separator illustrated in FIGS. 8 and 9.

Figure 10:
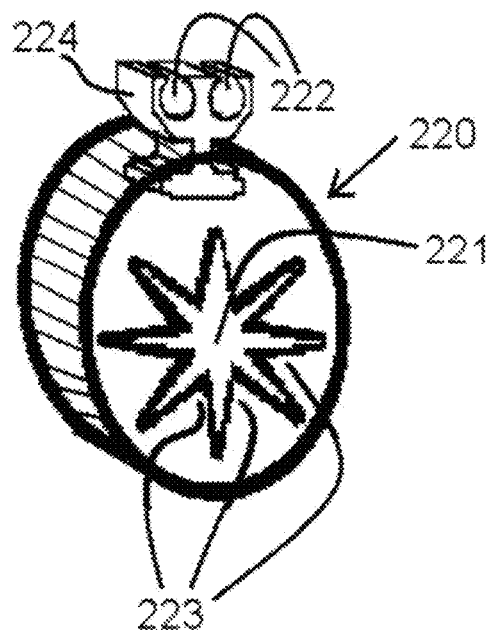

FIG. 10 illustrates a modification in the construction wherein the separator ring, therein generally designated 220, is integrated with the tubular probe received on a digit (finger or toe). The integrated digital probe/separator ring 220 also includes a hollow interior, as shown at 221, and is formed with the wedge-projections 223, corresponding to projections 23 and 123 in FIG. 8 and FIG. 9.

In FIG. 10, the fluid tubes (15, FIG. 1) are supported on a holder 224 attached to tubular probe/separator ring 220, and include longitudinally-extending grooves 222 formed in the upper surface of holder 223.

In all of the above-described constructions, the tubes are securely held by the tethering means, and thus mechanical perturbations of the tubes remote from the tethering site are prevented from being conducted to the probes. Likewise, all of the above described constructions, when applied in any of the locations with respect to the probe bearing digit illustrated in FIGS. 4-7 serve to physically separate and distance the neighboring digit or digits so that direct contact is avoided between the neighboring digits and the tubular socket probe on the measured digit on which the probe is mounted, or between any parts of the respectively neighboring digits. The avoidance of possible contact between the digit mounted probe and an adjacent digit, (finger or fingers), serves to eliminate mechanical perturbation of the probe which can seriously reduce the quality of the measured signals.

Another feature designed to improve the performance and ease of use of the measurement probes is a special means for quick reversible connection of the pressurized-fluid feed tubes of the system to the finger probes. This feature allows the pressurized-fluid tube connection to be quickly and easily effected in a manner requiring a minimum of operator effort or technical skill, while ensuring a stable and airtight connection. Further features of the tube connecting means are that it anchors the end portions of the tubes in a fixed, ordered, and stable arrangement, and that it elevates the tubes above the body surface.

Figure 11:
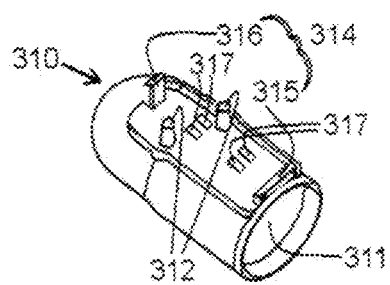
Figure 12:
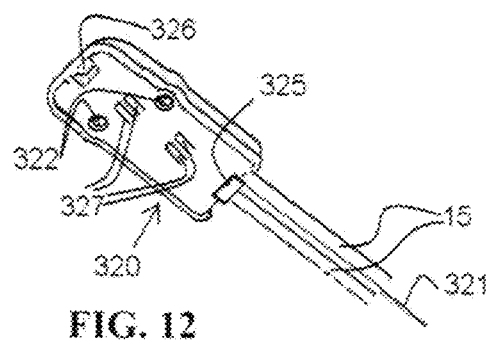

FIGS. 11-14 illustrate such a construction, including two main components namely a tubular socket-probe, generally designated 310 in FIG. 11 and a tube holder, generally designated 320 in FIG. 12 for attaching thereto the pressurized-fluid tubes 15. The tubular socket-probe 310 is formed with a hollow interior 311 for receiving the finger or toe of the subject, and with fluid conducting passageways terminating in inlet ports 312 for conducting the pressurized fluid, e.g. air, into the interior compartments of the probe. In addition to the foregoing, the probe 310 carries, on its upper surface, a mounting member 314 formed at one end with a latch, schematically indicated at 315, and at the opposite end with a locking element, schematically indicated at 316.

The apparatus illustrated in FIGS. 11-14 is particularly useful when it further includes an electrical device, such as an electrical heater, an optical plethysmograph, a temperature sensor, or the like. In such case, the probe 310 would include electrical contacts, schematically illustrated at 317, for the electrical device; and similarly, the tube holder 320 would also include electrical contacts, schematically indicated at 327, to engage electrical contacts 317 when the tube holder is applied to the integrated ring. The electrical conductors to which the electrical contacts 327 are connected are schematically shown at 321 in FIG. 12 (and as shown at 19 in FIGS. 1-7 inclusive). FIG. 12 also schematically illustrates the pressurized-fluid ports 322 to be coupled to ports 312 in the integrated ring 310, the latching element 325 to cooperate with latch 315 of the integrated ring, and the locking element 326 to engage locking element 316 of the integrated ring.

Figure 13:
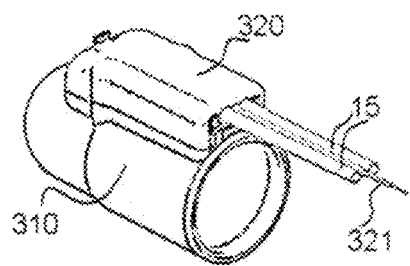

FIG. 11 illustrates the probe 310, when the air inlet ports 312 are in the form of rigid, slightly-fluted projections. Latch 315 within an internal recess, and a locking element 316 at the opposite end of the integrated ring, interact with their counterparts 325 and 326 respectively, in the removable tube mounting member 320, shown at FIG. 12. The air inlet ports 322 are preferably of an elastomeric material designed to be compressed upon application to the corresponding air inlet ports 312 on probe 310 to form an airtight seal, while the foregoing latch and locking elements interact to anchor and lock the two parts in a stable manner, yet releasable manner, as shown in FIG. 13. A further advantage of the two part connecting arrangement is that the electrical conducting wires, 321 similar to the fluid conducting tubes, are anchored in the end portion of mounting member 320 in a fixed and stable arrangement, likewise elevated above the body surface.

It will thus be seen that the construction illustrated in FIGS. 11-13 permits the fluid conducting tube and electrical connections to be quickly and easily effected in a manner requiring a minimum of operator effort or technical skill. It also assures a stable and airtight connection, and provides electrical connectors to enable electrical communication between the probe and the electrical device. Connections can thus be made, for example, to the elements of an optical plethysmograph, to a temperature sensing means, or to a heating coil, within the probe, as described above. Similarly, an electrical connection can be made to an electronic identification device mounted on the probe itself for the purpose of identifying the probe.

Figure 14:
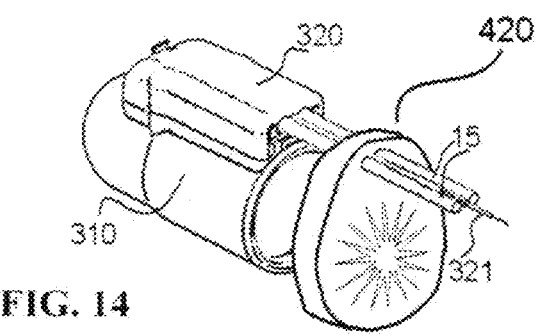

An advantageous combination of the tube and wire mounting means is depicted in FIGS. 12 and 13, and the finger separating and tube tethering means (shown for example in FIG. 2 as 20, in FIG. 3 as 120, and in FIG. 4 as 220), is depicted in FIG. 14. The elevation of the complex of conducting tubes and wires above the body surface from the distal end of the tube holder element 320 is illustrated in FIGS. 12 and 13.

There are a number of ways in which the probe and separator ring shown at 420 in FIG. 14 may interact, for example, by the formation of an arc of about 180° of the tubes and wires between the distal end of the tube holder element 320 and the tube retaining means of the separator ring 420. Likewise, the probe separator ring 420 may interact in the ways illustrated at FIG. 5 and FIG. 6, as briefly described above, in order to reduce the potential for mechanical perturbation of the probe due to mechanical strain, tugging or motion of the tubes and wires.

Figure 15:
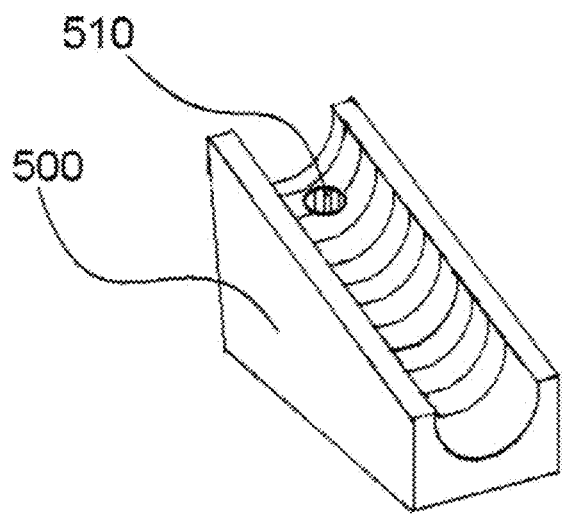
FIG. 15 illustrates an arm support including a mounting for a finger probe in accordance with the present invention.

FIG. 15 illustrates a further improvement in the monitoring apparatus of the present invention, which may be embodied in the limb support for supporting the limb of the digit of the subject's body to be monitored. In the illustrated embodiment of FIG. 15, the limb support is an arm support, generally designated 500, for supporting and stabilizing the forearm and base of the hand of the subject throughout the measurements, and allowing the digits to be comfortably and stably positioned in front of the limb support, thereby reducing patient movement and related mechanical perturbations and thus extraneous noise, where the digit to be monitored is one or more fingers of the subject's hand.

The forearm support illustrated in FIG. 15 is generally similar to that described in the above-cited U.S. Pat. No. 4,270,235 incorporated herein by reference, but has been modified by the provision of a probe-supporting recess 510 for supporting the pressure applicator 10, described above with respect to FIGS. 1-3, during the process of applying the probe to the patients digit. The modified forearm support illustrated in FIG. 15 thus facilitates the proper and stable placement of the pressure applicator on the patient's digit at an appropriate orientation to the digit, during the process of inserting the digit into the probe lumen, inflating, i.e., pressurizing, the probe.

The use of such an improved forearm support, in combination with the other devices described above with respect to FIGS. 1-14, provides a greater level of noise suppression than any of the individual devices alone.

Figure 16:
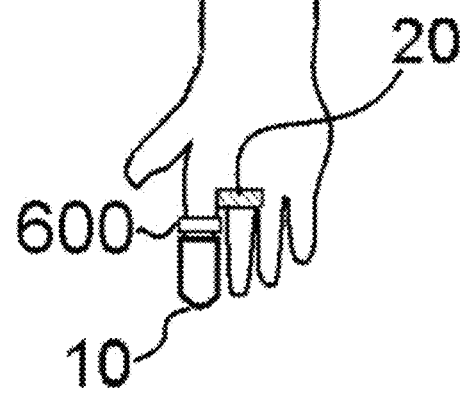
FIG. 16 illustrates another means for temporarily occluding the supply of blood to a measurement site in accordance with the present invention.

FIG. 16 illustrates another form of occlusion cuff, therein generally designated 600. It is applied to the finger carrying the pressure applicator 10 on the proximal side thereto, i.e., on the side thereof facing the subject's heart. In this case, the pressure applicator 10 itself may also serve as the occluder, instead of cuff 18 (FIG. 1).

Although it is usually possible to completely occlude blood flow, we have nevertheless discovered that in a fraction of cases, even very high levels of occlusion pressure, which may even be considerably higher than the patient's systolic blood pressure, are insufficient to entirely occlude the blood flow. This may be related to functional characteristics of the blood vessel structure and tissue composition. In such cases, the amplitude of the residual pulsatile blood volume signals is often unaffected by further increasing the level of applied occlusion pressure.

Under such circumstances, it is important to identify and quantify the occurrence of such incomplete occlusion, both in terms of the absolute and/or relative magnitude of the residual arterial pulsatile volumes, and also the absolute and/or relative duration of this incomplete occlusion during the prescribed occlusion period.

Such information is very important for determining the level of validity of a test, as a poor occlusion quality may adversely affect the degree of physiological stimulus in fact produced by the attempted occlusion. Thus the ability to detect and quantify the magnitude of the residual pulsatile signal present, despite a maximal allowed level of applied cuff pressure, is a further improvement of the current application. Determining the extent of the residual detected signal may for example provide information which is useful for categorizing the test quality, and thus for correcting the test result. It also provides feedback which is useful for limiting the pressure to be applied by the occluding means, in the event that with increasing pressure there is no further reduction in the degree of residual arterial pulse waves. The existence of incomplete occlusion despite the application of an above systolic pressure level, may in itself represent a significant diagnostic feature. In such apparatus, the monitoring probe is effective to monitor arterial pulse waves through the respective digit to indicate when there is no arterial pulse waves therethrough, or in the case where a complete occlusion cannot be effected, to produce a correction factor based on the residual signal magnitude, to be applied to the resulting signal following occlusion removal, and thus adjust the test result.

Figure 17:
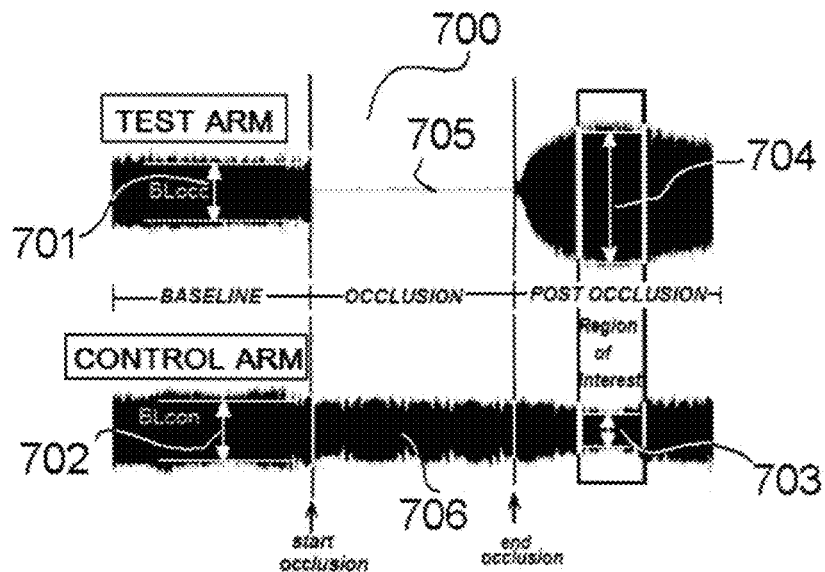
FIG. 17 illustrates an improved manner of making a baseline correction in accordance with the present invention.

The quantitative analysis of incomplete arterial occlusion may be determined by measuring the absolute amplitude of detected arterial pulse signals, as indicated 700 in FIG. 17, or by dividing the amplitude of detected arterial pulse signals, as indicated at 705 in FIG. 17, during occlusion by the corresponding arterial pulse signals, as indicated at 706, or by for example the mean amplitude of the occluded side baseline arterial pulse signals amplitude as indicated at 701 or 704. The resulting ratios can thus provide relative indices of incomplete arterial occlusion, when their value exceeds a predetermined threshold value.

Likewise, the absolute value of arterial pulse signals at 705 can be used to identify an absolute index of incomplete arterial occlusion when the value of said absolute index of incomplete arterial occlusion exceeds a predetermined threshold value. Furthermore, the said absolute or relative indices of incomplete arterial occlusion may be used to categorize the test quality, and to correct the test result.

Figure 18:
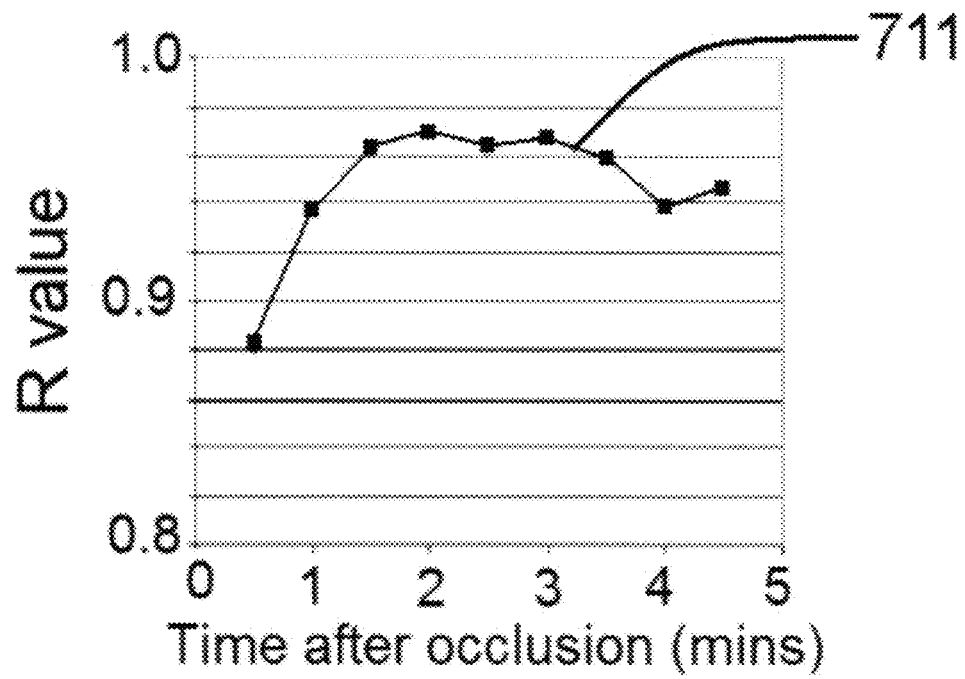
FIGS. 18 and 19 illustrate correlation diagrams relevant to variations of FIG. 17.

U.S. Pat. No. 6,939,304, FIG. 16, described a strikingly powerful relationship linking the pre-occlusion arterial pulse wave signal amplitude with subsequent relative signal amplitude change following a standard period of blood flow occlusion. This relationship has been consistently observed in large study populations, and importantly, it is consistently observed when considering multiple tests within a given individual subject, where considerable variability of the pre-occlusion signal amplitude may be observed, suggesting that such variability is physiologically normal. As shown in FIG. 18, the post-occlusion, relative signal amplitude change has been found to be exponentially inversely related to the pre-stimulus signal amplitude, and has subsequently been found to have a remarkably high correlation coefficient of around 0.8 in large samples of n>1,000. Essentially this means that a lower amplitude pre occlusion signal is associated with a larger relative increase following the release of the occlusion, and vice versa. Since a pre-stimulus signal amplitude may be widely variable due to normal physiological factors, even within an individual, the consequent post-occlusion relative signal amplitude change variability may thus also be considered to be physiologically normal. Since a post-occlusion relative signal amplitude change is indicative of endothelial function, its potential instability related to physiologically normal variability of the pre-occlusion baseline amplitude raises a problem, because endothelial function in an individual is assumed to be stable at least in the short term. This problem can be resolved by using an empirically derived correction factor to be applied for correcting for this inherent baseline amplitude dependency of the post occlusion response.

Such a baseline signal amplitude related correction factor was described in U.S. Pat. No. 6,939,304. It is essentially a reciprocal function to the correlation function between baseline signal amplitude and post occlusion signal amplitude changes. It is applied to a given baseline signal amplitude to yield a correction factor, and is of the basic form: Correction factor=a*log Baseline amplitude +b, where the baseline value is the pre-occlusion signal amplitude.

The present application describes a number of improvements to this correction factor, based on temporal adjustment, tissue volume, and blood pressure related corrections of the pre-occlusion baseline amplitude used in determining the correction factor.

Figure 19:
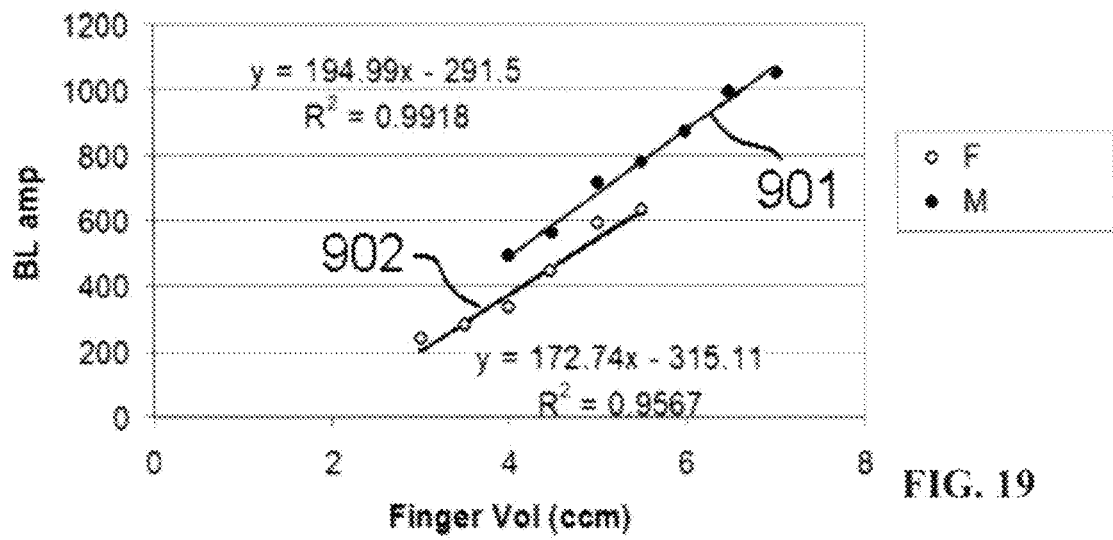

The finger and toe arteries are particularly responsive to autonomic nervous system activity. This is itself subject to spontaneous change over time in general, and is highly reactive to noxious stimuli such as a period of blood flow occlusion FIG. 18 shows the results of a study comparing the simultaneously measured response indices corresponding to 704/701 described in FIG. 7 when a cuff was used to apply the occlusion pressure field on one side while the identical pressure field was applied within a probe on the opposite sided digit. This study comprised 40 subjects as can be seen in FIG. 13, the correlations over successive 30 second epochs of time after the end of occlusion shown at 801, were consistently extremely high. The subjective impression all 40 subjects was that the digit applied occlusion was considerably less uncomfortable than the cuff applied occlusion. Thus, effecting the occlusion within the probe itself may be advantageous, however both means of producing arterial occlusion are considered to be effective and clinically acceptable. FIG. 19 shows the results of a study comparing finger volume versus baseline amplitude wherein lines 901 and 902 indicating the male and female relationships are highly correlated, linear and parallel.

Thus, it would be reasonable to expect this stimulus to transiently change the finger and toe vascular tone, and therefore the measured baseline amplitude, when comparing the pre-occlusion and post occlusion periods. Unfortunately, it is not possible to accurately measure the signal amplitude of the occluded site after occlusion since the occlusion itself induces local changes in its aftermath at the occluded site, greatly affecting the signal. U.S. Pat. No. 6,939,304 described using the unadjusted pre occlusion period baseline amplitude of the occluded side as a basis for correction, despite the likelihood that the actual signal amplitude could have been substantially affected by normal autonomic nervous system related factors associated with the occlusion event.

FIG. 17 shows, amongst other things, a way in which such a correction to assess the above mentioned autonomically mediated changes could be made indirectly, based on using the ratio of post-occlusion to pre-occlusion changes of the un-occluded site (control) signal, to appropriately compensate the occluded site baseline signal amplitude.

This process is explained as follows:

Firstly, when considering the overall time course of a representative test study, indicated in FIG. 17 generally as 700, an occluded site response ratio can be determined by dividing the measured post occlusion signal amplitude 704, by its baseline signal amplitude 701. Similarly, an un-occluded site response ratio can be determined by dividing the measured post occlusion signal amplitude 703, by its baseline signal amplitude 702. When the occluded site ratio is divided by its corresponding and simultaneously recorded un-occluded site response ratio, this yields a corrected ratio, as indicated at A in FIG. 17.

Multiplying this corrected ratio by the above described baseline amplitude correction factor, of the general form a*log 701+b where a and b are constants, yields a baseline amplitude corrected ratio, as indicted at B in FIG. 17.

To effect a temporal correction to the baseline amplitude correction factor, the baseline amplitude in the region of interest during the pre-occlusion period of the site to be occluded indicated as 701, may be corrected by being multiplied by the ratio of the un-occluded (control), site post occlusion signal amplitude (703) divided by the control site pre-occlusion signal amplitude (702), to determine a temporally corrected baseline amplitude, and substituting this value into the baseline correction factor function to derive a temporally adjusted baseline correction factor. Thus, substituting (701*(703/702)) into the baseline correction factor function and multiplying by corrected ratio yields a temporally adjusted baseline amplitude corrected ratio, as indicated at C in FIG. 17.

Alternatively, the same type of correction may be made using the control side post-occlusion signal amplitude immediately before the time of the region of interest, such that the corrected occluded side baseline would represent the adjusted signal amplitude immediately before the elected region of interest time. Applying such a correction to the measured pre occlusion occluded site baseline data for in a group of 732 subjects increased its correlation to the subsequent post occlusion vascular response.

For instance, it was found that the linear regression correlation coefficient between the logarithm of the pre occlusion occluded site baseline amplitude 701, and the corrected ratio i.e. (704/701)/(703/702), was 0.755, while the correlation to the occluded side pre-occlusion amplitude (701) after being corrected by being multiplied by the ratio of 803/802, was 0.848.

A further shortcoming of the baseline amplitude correction factor described in U.S. Pat. No. 6,939,304, is that it did not take into account the actual tissue volume of the finger from which it was derived. This is important when considering the signal amplitude/post-occlusion response relationship. Thus, what is important is the level of vascular tone upon which the stimulus is being applied, rather than the signal size as such. The degree of vascular tone is determined by the relative degree of vascular resistance which is in turn related to the signal amplitude normalized to the tissue volume from which it is derived. Since finger size varies substantially between people, and even between fingers of the same hand (e.g. thumb vs. little finger), this could be expected to impact on the accuracy of the baseline amplitude correction function mentioned above. FIG. 19 shows the average baseline amplitude values associated with given interval ranges of the estimated volume of the distal phalanx of a finger volume, based on measurement of the actual finger perimeter, with 901 representing the male population and 902 representing the female population, together with respective lines of best fit (least squares) and respective linear regression coefficients. The plots demonstrates both the linearity of finger size vs. signal baseline amplitude (corresponding to 701 in FIG. 17), as well as the span of finger sizes, based on a population of 1959 males and 1266 females, grouped by the estimated volume intervals based on the perimetry measurements. It also appears that there is a gender related offset with males having larger amplitudes compared to females at a given finger volume, which may be related to physiological factors or to anatomical factors.

When baseline signal amplitude was corrected for the temporal delay as defined above, and further normalized by dividing the baseline signal amplitude by the measured tissue volume itself divided by a reference tissue volume value, its subsequent correlation to the corrected ratio i.e. (704/701)/(703/702), was increased to 0.8550.

Determining the digit tissue volume for the above described tissue volume based source of inaccuracy could be resolved by normalizing the measured signal to the actual finger size. An automated method for quantitatively determining tissue volume is described in U.S. Pat. No. 7,819,811. However, that method for implementing this measurement requires major changes to the apparatus. FIG. 18 shows the results of a study comparing the simultaneously measured response indices corresponding to 704/701 described in FIG. 17, when a cuff was used to apply the occlusion pressure field on one side, while the identical pressure field was applied within a probe on the opposite sided digit. This study comprised 40 subjects. As can be seen in FIG. 18, the correlations over successive 30 second epochs of time after the end of occlusion shown at 711, were consistently extremely high. The subjective impression all 40 subjects was that the digit applied occlusion was considerably less uncomfortable than the cuff applied occlusion. Thus, effecting the occlusion within the probe itself may be advantageous, however both means of producing arterial occlusion are considered to be effective and clinically acceptable.

Figure 20:
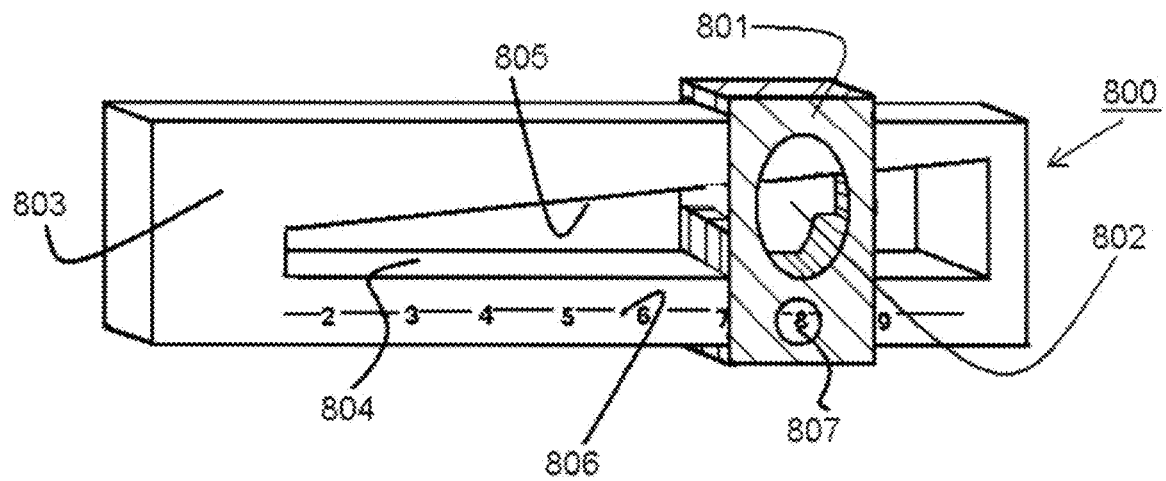
FIG. 20 illustrates a digit-size measuring device that may be included in the improved apparatus for measuring tissue volume to provide a baseline correction in accordance with the present invention.

FIG. 20 illustrates a digit-size measuring device, therein generally designated 800, for measuring the size of the distal end of the digit to produce a corrected baseline correction factor based on the volume of the distal end of the digit. As shown in FIG. 20, device 800 includes a digit-receiving member 801 formed with an opening 802 for receiving the digit. Member 801 is slidable along another member 803 which includes side surfaces 804 and 805 intersecting at an acute angle and engaged by the outer surface of the digit received within member 801. Member 803 is further formed with a scale 806 along surface 804. Scale 806 is graduated to indicate the size of the digit, and thereby its volume, when the digit is moved along member 803 until the outer surfaces of the digit come into contact with both surfaces 804 and 805 of member 803. The scale is viewable through a window 807 formed in a side wall of member 801.

The design shown in FIG. 20 merely serves to illustrate a simple means for measuring the finger size at a given region of the finger's length with respect to its distal extremity. Numerous other means could be used to this end, including but not limited to a direct measurement of the digit perimeter using a measuring tape, a series of holes of varying sizes to determine the smallest size capable of allowing the digit region to enter it.

Another alternative approach to adjusting the baseline signal amplitude is to normalize signal amplitude to the subjects Body Surface Area, (BSA), itself divided by a reference BSA value, which can be derived from the subject's height and weight using well known formulae. Since this is significantly correlated to finger tissue volume, it can be used as a surrogate of volume to aid in normalizing the baseline signal amplitude in the manner shown in FIG. 17 at D.

The above describe examples, which are merely illustrative, would provide a finger size surrogate index, as opposed to a rigorous determination of volume as per our U.S. Pat. No. 7,819,811, but would have the advantage of being simply applied.

Similar to the correction of the signal amplitude based on the tissue volume, it may also be advantageous to correct the baseline signal amplitude with respect to the span of the patient's pulse pressure, that is the difference between systolic and diastolic systemic blood pressure. The pulse pressure acts in concert with the level of effective arterial resistance to determine the resulting signal amplitude.

The reason why it may be advantageous to correct the signal amplitude for pulse pressure magnitude is that, when considering the interaction between the initial signal amplitude and the post occlusion response, what is really important is the level of vascular tone upon which the stimulus is being applied, rather than the signal size as such. Since the magnitude of a subjects pulse pressure is derived from the combination of the action of the heart and the overall systemic resistance, it is, to a large extent, independent of the local vascular resistance of the specific measurement site under consideration. Thus, variations in pulse pressure at a given level of localized vascular tone could give rise to substantial variations in the signal amplitude, and this could thus be expected to impact on the accuracy of the baseline amplitude determination. A subject with a large pulse pressure would thus be expected to exhibit a lower level of arterial tone, and thus a greater capacity for vasodilation, compared to one having the same signal amplitude but with a smaller pulse pressure.

A process of normalization of the baseline signal amplitude would thus be based on correcting the measured baseline signal amplitude by the ratio of the patient's pulse pressure to a reference pulse pressure value, as shown in FIG. 17 at E.

Another analysis feature, unexpectedly discovered to be useful in improving the diagnostic performance, is that of applying a logarithmic transformation to the response indices described in FIG. 17 at A, B, C, D and E. Using the log of the response index has been empirically demonstrated to provide better separation between patient and unselected populations than the corresponding conventional index. Since it provides a less skewed frequency distribution profile, it also would appear to be a statistically appropriate change.

The "Augmentation Index" is a well known index which uses the noninvasively measured pulse wave shape to provide a parameter that reflects the general level of arterial stiffness, the increase of which is amongst other things, a consequence of arterial aging and arteriosclerosis. The pulse wave shape is affected by the degree to which the incident central arterial pressure is changed by its summation with wave reflection of the pulse wave. Degeneration of the arterial wall due to aging and disease processes results in a stiffening of the arterial walls and in an increase in the pulse wave velocity, which affect the manner in which the incident and reflected waves summate.

The PAT probe provides a uniquely advantageous measurement environment for measuring this index. This is due to its ability to restrict the measurement solely to arterial pulse waves without venous admixture, while further ensuring that the site of measurement is not affected by induced venous pooling which can induce reflex vascular changes. It further ensures that a state of optimal transmural pressure is applied to the measurement to optimally unload the arterial wall tension and thereby provide the optimal range of vascular motion and signal linearity, as described in considerable detail in for example U.S. Pat. No. 6,319,205. Thus, using the PAT apparatus and method facilitates the accurate and consistent measurement of the Augmentation index.

Many other variations, modifications and applications of the invention will be apparent to those skilled in the art.

What is claimed is:

1. Apparatus for monitoring arterial pulse waves of a subject comprising:
    first and second probes for respective application to first and second probe-receiving digits of one or more limbs of said subject, wherein each of the first and second probes carries at least in part a measuring device configured for measuring signals from said arterial pulse waves flowing through the respective first and second probe-receiving digits;
    for each of the first and second probes:
        a fluid conducting feed tube attachable to said first or second probe, and
        a separator ring, receivable on a supporting digit, said supporting digit is selected from a group consisting of the probe-receiving digit and a digit adjacent to the probe-receiving digit, and configured for securing thereto and supporting said fluid conducting feed tube;
        wherein said separator ring:
            being sized to distance said first or second probe from at least one digit adjacent to said respective first or second probe-receiving digit so as to prevent contact therebetween, and
            having an inner surface formed with a plurality of longitudinally-extending, circumferentially-spaced ribs with intervening gaps;
            wherein said circumferentially-spaced ribs are configured to be of sufficient resilience to support said fluid conducting feed tube above said supporting digit, while applying localized force of a level low enough to ensure that flow of both venous and arterial blood is not adversely affected in said supporting digit; and
    a processor;
    wherein:
    each of the first and second probes comprises a tubular socket, and a pressure applicator having at least one portion;
    the pressure applicator of each of the first and second probes is configured to apply a respective static pressure field to enclose at least a distal phalanx of said respective first or second probe-receiving digit, including an outer-most tip thereof, received in said tubular socket of said first or second probe;
    the pressure applicator of the first probe also includes a portion of the at least one portion configured to apply an occlusion by an interrupted occluding pressure field to at least the distal phalanx of the first probe-receiving digit, or to a region between said at least the distal phalanx of the first probe-receiving digit and the subject's heart;
    the processor is configured to control said interrupted occluding pressure field and respective static pressure fields in response to output of the measuring devices of the first and second probes for each of predetermined periods: before said occlusion, during said occlusion, and after said occlusion, wherein an extent of residual detected arterial pulse signal, which indicates an incomplete arterial occlusion, provides feedback to the processor effective to increase pressure during said occlusion such that there is no further reduction in a degree of residual arterial pulse waves;

the processor is further configured to calculate an adjusted baseline amplitude corrected ratio using an occluded site ratio and an un-occluded site ratio by:
- (a) for an occluded site of the first probe-receiving digit occluded by the interrupted occluding pressure field, dividing an amplitude of arterial pulse waves during the predetermined period after occlusion by an amplitude of arterial pulse waves during the predetermined period before occlusion to provide the occluded site ratio,
- (b) calculating the un-occluded site ratio for an un-occluded site of the second probe-receiving digit by: dividing an amplitude of arterial pulse waves during the predetermined period after occlusion or dividing an amplitude of arterial pulse waves during a period before the predetermined period after occlusion but after the predetermined period during occlusion, by an amplitude of arterial pulse waves during the predetermined period before occlusion,
- (c) dividing the occluded site ratio by the un-occluded site ratio to provide a corrected ratio,
- (d) calculating an adjusted baseline amplitude by modifying a baseline amplitude of the arterial pulse waves of the occluded site during the predetermined period before occlusion, by a ratio selected from a group consisting of:
  - a ratio between tissue volume of the first probe-receiving digit of the subject and a reference tissue volume,
  - a ratio between pulse pressure of the subject and a reference pulse pressure, and
  - the un-occluded site ratio, and
- (e) adjusting the corrected ratio by a logarithmic transformation of the adjusted baseline amplitude, to provide the adjusted baseline amplitude corrected ratio as a measure of endothelial function in the subject.

2. The apparatus according to claim 1, wherein: said first and second probe-receiving digits are on separate limbs of said subject.

3. The apparatus according to claim 1, wherein, for at least one of said first and second probes, said fluid conducting feed tube passes through a bore formed longitudinally through said separator ring laterally of said circumferentially-spaced ribs, on a side of said separator ring configured to face a dorsal surface of the respective first or second probe-receiving digit such that said fluid conducting feed tube is elevated above the dorsal surface.

4. The apparatus according to claim 1, wherein, for at least one of the first and second probes, said separator ring is formed, on its outer surface, with a longitudinally-extending groove on one or both sides each for receiving a digit of the subject's body adjacent to the supporting digit.

5. The apparatus according to claim 1, wherein, for at least one of said first and second probes, said fluid conducting feed tube and at least one electrical wire configured as a portion of an interconnection communicating an output of the measuring device to the processor are connected to, or pass through, a bore formed longitudinally through said separator ring laterally of said circumferentially-spaced ribs, on a side of said separator ring configured to face a dorsal surface of the respective first or second probe-receiving digit, effective to support, to tether, and to elevate said fluid conducting feed tube and at least one electrical wire above the dorsal surface.

6. The apparatus of claim 5, wherein said to tether and to elevate said fluid conducting feed tube and at least one electrical wire is effective to reduce mechanical perturbation of the at least one of said first and second probes due to tugging, strain or motion of the fluid conducting feed tubes or at least one electrical wire on said at least one of said first and second probes.

7. The apparatus according to claim 1, wherein said processor is further configured:
- to receive signals from said first and second probes; and
- to provide an output indicating a peripheral arterial tone of the subject based on said signals.

8. An apparatus for monitoring arterial pulse waves of a subject comprising:
- a first probe for application to a first probe-receiving digit of a limb of said subject, and a second probe for application to a second probe-receiving digit, each of the first and second probes comprising:
  - a tubular socket,
  - a measuring device configured for measuring signals from said arterial pulse waves flowing through the first or second probe-receiving digit, and
  - a pressure applicator having at least one portion;
- wherein the pressure applicator of each of the first and second probes is configured to apply a static pressure field to enclose at least a distal phalanx of the first or second probe-receiving digit, including an outer-most tip thereof, received in the tubular socket; and
- wherein the pressure applicator of the first probe includes a portion of the at least one portion configured to apply an occlusion by an interrupted occluding pressure field to at least the distal phalanx of the first probe-receiving digit, or to a region between said at least the distal phalanx of the first probe-receiving digit and the subject's heart;
- a processor configured to control the interrupted occluding pressure and static pressure fields in response to output of the measuring devices, for each of predetermined periods: before said occlusion, during said occlusion, and after said occlusion for at least one period of occlusion, wherein an extent of residual detected arterial pulse signal which indicates an incomplete arterial occlusion, provides feedback to the processor effective to increase pressure during said occlusion such that there is no further reduction in a degree of residual arterial pulse waves;

wherein:
the processor is further configured to calculate an adjusted baseline amplitude corrected ratio using an occluded site ratio and an un-occluded site ratio by:
- (a) for an occluded site of the first probe-receiving digit occluded by the interrupted occluding pressure field, dividing an amplitude of arterial pulse waves during the predetermined period after occlusion by an amplitude of arterial pulse waves during the predetermined period before occlusion to provide the occluded site ratio,
- (b) calculating the un-occluded site ratio for an un-occluded site of the second probe-receiving digit by: dividing an amplitude of arterial pulse waves during the predetermined period after occlusion or dividing an amplitude of arterial pulse waves during a period before the predetermined period after occlusion but after the predetermined time period during occlusion, by an amplitude of arterial pulse waves during the predetermined period before occlusion,
- (c) dividing the occluded site ratio by the un-occluded site ratio to provide a corrected ratio, (d) calculating an adjusted baseline amplitude by modifying a baseline amplitude of the arterial pulse waves of the occluded site during the predetermined period before occlusions by a ratio selected from a group consisting of:
a ratio between tissue volume of the first probe-receiving digit of the subject and a reference tissue volume,
a ratio between pulse pressure of the subject and a reference pulse pressure,
a ratio between the arterial pulse signal amplitude at the un-occluded site during a period after said occlusion but before the predetermined period after said occlusion, and arterial pulse signal amplitude during the predetermined period before occlusion, and
the un-occluded site ratio, and
(e) adjusting the corrected ratio by a logarithmic transformation of the adjusted baseline amplitude, to provide the adjusted baseline amplitude corrected ratio as a measure of endothelial function in the subject.

9. The apparatus according to claim 8, wherein said pressure applicator of at least one of the first and second probes applies a pressure sufficient to substantially prevent venous pooling and to partially unload wall tension of, but not to occlude, the arteries in at least one of the first or second probe-receiving digits including at least the distal phalanx.

10. The apparatus according to claim 8, wherein said processor is configured to receive signals from said first and second probes and to provide an output indicating an augmentation index of the subject, based on a pulse wave shape of the received signals.

11. The apparatus according to claim 8, wherein, for each of the first and second probes, said measuring device is selected from among a group consisting of:
a volumetric change measurement device, an optical density measurement device, a surface-reflectivity measurement device, a pulse oximetry measurement device, an electrical resistivity measurement device, a Doppler ultrasound measurement device, a laser Doppler measurement device, a flow meter device, a segmental plethysmograph, a circumferential strain gauge device, an optical plethysmograph, an isotope washout device, a thermal washout device, a temperature measurement device, an electromagnetic measurement device, a sensor affected by a change in finger geometry or red blood cell alignment or flux associated with pulsatile volume changes, and a Hall effect sensor.

12. The apparatus according to claim 8, wherein:
the processor is further configured to calculate and provide an index of incomplete arterial occlusion effective to categorize a test quality and to correct a test result by:
for an incompletely occluded site of the first probe-receiving digit incompletely occluded by the interrupted occluding pressure field, dividing an amplitude of arterial pulse waves of the incompletely occluded site during the predetermined occlusion period by one of:
(a) an amplitude of corresponding arterial pulse waves of an un-occluded site of the second probe-receiving digit, and
(b) an average amplitude of arterial pulse waves of the before-occlusion period of the occluded site;
to provide the index of incomplete arterial occlusion.

13. The apparatus according to claim 8:
wherein the processor is further configured to calculate and provide an index of incomplete arterial occlusion effective to categorize a test quality and to correct a test result by:
for an incompletely occluded site of the first probe-receiving digit incompletely occluded by the interrupted occluding pressure field,
providing an absolute amplitude of arterial pulse waves of the incompletely occluded site during the predetermined occlusion period as the index of incomplete arterial occlusion.

14. The apparatus of claim 8, wherein the portion of the at least one portion of the pressure applicator of the first probe configured to apply the occlusion by the interrupted occluding pressure field comprises an occluding cuff sized to be applied to the limb of the subject.

15. A method of monitoring arterial pulse waves of a subject comprising:
receiving, from a first and second probe applied to respective first and second probe-receiving digits of one or more limbs of said subject, measurements of interrupted occluding and static pressure fields, including measurements of arterial pulse waves, for each of predetermined periods: before occlusion, during occlusion, and after occlusion;
wherein each of the first and second probes comprises:
a tubular socket,
a measuring device configured for measuring signals from said arterial pulse waves flowing through the respective first and second probe-receiving digit, and
a pressure applicator having at least one portion;
wherein the pressure applicator of each of the first and second probes is configured to apply the static pressure field to enclose at least a distal phalanx of the respective first and second probe-receiving digit, including an outer-most tip thereof, received in the tubular socket; and
wherein the pressure applicator of the first probe includes a portion of the at least one portion configured to apply an occlusion by the interrupted occluding pressure field to at least the distal phalanx of the first probe-receiving digit, or to a region between said at least the distal phalanx of the first probe-receiving digit and the subject's heart, wherein an extent of residual detected arterial pulse signal which indicates an incomplete arterial occlusion, provides feedback to control said pressure applicator effective to increase pressure during said occlusion such that there is no further reduction in a degree of residual arterial pulse waves;
calculating an adjusted baseline amplitude corrected ratio using an occluded site ratio and an un-occluded site ratio, wherein the calculating comprises:
(a) for an occluded site of the first probe-receiving digit occluded by the interrupted occluding pressure field, dividing an amplitude of arterial pulse waves during the predetermined period after occlusion by an amplitude of arterial pulse waves during the predetermined period before occlusion to provide the occluded site ratio,
(b) calculating the un-occluded site ratio for an un-occluded site of the second probe-receiving digit by: dividing an amplitude of arterial pulse waves during the predetermined period after occlusion or dividing an amplitude of arterial pulse waves during a period before the predetermined period after occlusion but after the predetermined period during occlusion, by an amplitude of arterial pulse waves during the predetermined period before occlusion,
(c) dividing the occluded site ratio by the un-occluded site ratio to provide a corrected ratio,
(d) calculating an adjusted baseline amplitude by modifying a baseline amplitude of the arterial pulse waves of the occluded site during the predetermined period before occlusions by a ratio selected from a group consisting of:
  a ratio between tissue volume of the first probe-receiving digit of the subject and a reference tissue volume,
  a ratio between pulse pressure of the subject and a reference pulse pressure, and
  the un-occluded site ratio, and
(e) adjusting the corrected ratio by a logarithmic transformation of the adjusted baseline amplitude, to provide the adjusted baseline amplitude corrected ratio; and
providing the adjusted baseline amplitude corrected ratio as a measure of endothelial function in the subject.

16. The method of claim 15, comprising
inserting into each of the first and second probes the at least distal phalanx of the respective first and second probe-receiving digit of said subject, including the outer-most tip thereof;
applying the static pressure field to each said at least distal phalanx;
applying the interrupted occluding pressure field to the region between the outer-most tip of the first probe-receiving digit and the heart of said subject; and
measuring said arterial pulse waves from said first and second probe-receiving digits.

17. The method of claim 16, wherein said first and second probe-receiving digits are mutually non-adjacent on one limb of said subject, and said interrupted occluding pressure field is applied to a region of said first probe-receiving digit.

18. The method of claim 16, wherein said first and second probe-receiving digits are on opposite limbs of said subject.

19. The method of claim 16, wherein said measuring said arterial pulse waves comprises using the measuring devices of said first and second probes, said measuring devices being selected from among a group consisting of:
  a volumetric change measurement device, an optical density measurement device, a surface-reflectivity measurement device, a pulse oximetry measurement device, an electrical resistivity measurement device, a Doppler ultrasound measurement device, a laser Doppler measurement device, a flow meter device, a segmental plethysmograph, a circumferential strain gauge device, an optical plethysmograph, an isotope washout device, a thermal washout device, a temperature measurement device, an electromagnetic measurement device, a sensor affected by a change in finger geometry or red blood cell alignment or flux associated with pulsatile volume changes, and a Hall effect sensor.

20. The method according to claim 16, comprising:
applying at least one separator ring to a respective supporting digit for each of the first and second probes applied to respective first and second probe-receiving digits, such that each of the first and second probe-receiving digits is adjacent to the respective supporting digit, said applying including attaching to said at least one separator ring a fluid feed tube leading from said first or second probe;
wherein said at least one separator ring is configured with sufficient resilience to support said feed tube on said respective supporting digit, while applying localized force of a level low enough to ensure that flow of both venous and arterial blood is not adversely affected in said respective supporting digit.

\* \* \* \* \*